United States Patent [19]

Miller et al.

[11] Patent Number: 5,636,630
[45] Date of Patent: Jun. 10, 1997

[54] RESPIRATORY DEVICE AND METHOD THEREFOR

[76] Inventors: Wallace T. Miller, 13002 N. 31 Dr.; Carmen Caccavale, 7117 W. Foothill Dr., both of Phoenix, Ariz. 85029

[21] Appl. No.: 684,877

[22] Filed: Jul. 25, 1996

[51] Int. Cl.$^6$ ..................................................... A61M 31/00
[52] U.S. Cl. ............................... 128/207.17; 128/207.18; 128/200.26
[58] Field of Search .......................... 128/200.26, 200.28, 128/202.27, 207.17, 207.18, 911, 912, DIG. 26, 206.27, 207.11

[56] References Cited

U.S. PATENT DOCUMENTS

| | | | |
|---|---|---|---|
| 2,931,358 | 4/1960 | Sheridan | 128/207.18 |
| 3,400,714 | 9/1968 | Sheridan | 128/207.18 |
| 3,643,660 | 2/1972 | Hudson et al. | 128/207.18 |
| 3,726,275 | 4/1973 | Jackson et al. | 128/207.18 |
| 3,802,431 | 4/1974 | Farr | 128/207.18 |
| 4,106,505 | 8/1978 | Salter et al. | 128/207.18 |
| 4,278,082 | 7/1981 | Blackmer | 128/207.18 |
| 4,406,283 | 9/1983 | Bir | 128/207.18 |
| 4,648,398 | 3/1987 | Agdanowski et al. | 128/207.18 |
| 4,915,105 | 4/1990 | Lee | 128/207.18 |
| 5,046,491 | 9/1991 | Derrick | 128/207.18 |

*Primary Examiner*—Vincent Millin
*Assistant Examiner*—Robert N. Wieland
*Attorney, Agent, or Firm*—Harry M. Weiss; Jeffrey D. Moy; Harry M. Weiss & Associates, P.C.

[57] ABSTRACT

A respiratory device and method of operating the same are shown comprising, in combination, a conduit portion passing above a user's left and right ears and which is coupled to the user's nostrils for supplying a fluid to the user, and a coupling portion contacting a back portion of the user's head and having a cavity through which the conduit portion passes for securely coupling the conduit portion around part of the user's head. The conduit portion comprises a plurality of flexible, tubular members which are coupled to a nasal cannula inserted into the user's nostrils. The tubular members criss-cross within the cavity, thereby securing the cannula to the user's nostrils without, as was previously done, having the members painfully wrapped around the user's ears.

16 Claims, 1 Drawing Sheet

RESPIRATORY DEVICE AND METHOD THEREFOR

BACKGROUND OF THE INVENTION

1. Field of the Invention

This invention is in the field of respiratory devices and methods therefor and, more particularly, is a respiratory device for supplying a fluid, such as oxygen, to a user's nostrils without the need of wrapping oxygen supply lines around the user's ears to secure the device, and a method therefor.

2. Description of the Related Art

Oftentimes a patient will require a continuous oxygen supply while at a medical facility or while at home under medical care. Oxygen delivery devices, such as the cannula, are well known in the medical arts. The typical means and method for attaching an oxygen supply cannula to a patient's nostrils involves attaching a pair of oxygen supply lines to the cannula, and inserting the appropriate portions of the cannula into the patient's nostrils. Next, the oxygen supply lines are wrapped around the patient's ears, and the remaining portions of the oxygen supply lines are left to hang below the patient's chin, where an adapter couples the two oxygen supply lines into a single oxygen supply line. Additionally, below the chin of the patient, most systems use a slide connector to hold the two supply lines snugly against the patient's chin.

The problems with the prior art arrangement are many and significant. First, the reason that the oxygen supply lines are wrapped around the patient's ears is to provide a support for the oxygen supply lines, as well as for the cannula attached thereto. Thus, in order to have the cannula smartly fitted into the patient's nostrils, as desired, the oxygen supply lines are typically wrapped quite tightly about the patient's ears, and this is very painful for the patient. In response, some patients use a cushion around portions of their ears in order to mitigate the pain associated with having the oxygen supply lines so tightly tethered to their ears.

Another serious problem associated with the typical cannula oxygen supply system described above, and with other previous designs, is that the cannula has a tendency to fall out of the patient's nostrils. For some patients, this is simply unacceptable. Thus, they wrap the oxygen supply lines around their ears extremely tightly, and they snug the lower portions of the oxygen supply lines very firmly against the chin. Accordingly, the pain suffered by these patients is even greater than that normally experienced by the user; however, for a patient who must have the oxygen supply attached at all times, such pain is reluctantly accepted.

Therefore, there existed a need to provide a device for comfort, yet reliably attaching an oxygen cannula to a patient's nostrils, without the need for wrapping oxygen supply lines around the patient's ears.

SUMMARY OF THE INVENTION

An object of the present invention is to provide an improved respiratory device including an oxygen supply cannula and a method therefor.

Another object of the present invention is to provide an improved respiratory device wherein the supply lines to an oxygen supply cannula are not attached around the patient's ears and a method therefor.

Still another object of the present invention is to provide an improved respiratory device including an oxygen supply cannula which is more reliably and comfortably coupled to the patient's nostrils and a method therefor.

BRIEF DESCRIPTION OF THE PREFERRED EMBODIMENTS

According to the present invention, a respiratory device is disclosed comprising, in combination, conduit means passing above a user's left and right ears and coupled to the user's nostrils for supplying a fluid to the user, and coupling means contacting a back portion of the user's head and having a cavity through which the conduit means passes for securely coupling the conduit means around a portion of the user's head. The conduit means criss-crosses within the cavity in order to provide additional tension to hold the device securely around the user or patient's head. The device further includes a nasal cannula coupled to the conduit means.

The conduit means comprises a plurality of flexible, tubular members independently coupled to the nasal cannula. Moreover, each member of the plurality of flexible, tubular members is greater than 21 inches in length. The coupling means comprises a compressible member having the cavity passing therethrough. The position of the coupling means along the conduit means is adjustable by sliding the coupling means along the conduit means until a desired position is attained and the conduit means is criss-crossed within the cavity for holding the conduit means around the previously mentioned portion of the user's head. Generally, the coupling means is located below the user's left and right ears, while the fluid comprises oxygen gas or other gas suitable for delivery to the nostrils of a patient. The cavity comprises a single, tubular cavity in substantial vertical alignment with a vertical axis of the user's head.

The foregoing and other objects, features, and advantages of the invention will be apparent from the following, more particular, description of the preferred embodiments of the invention, as illustrated in the accompanying drawings.

DESCRIPTION OF THE PREFERRED EMBODIMENTS

Figure 1:
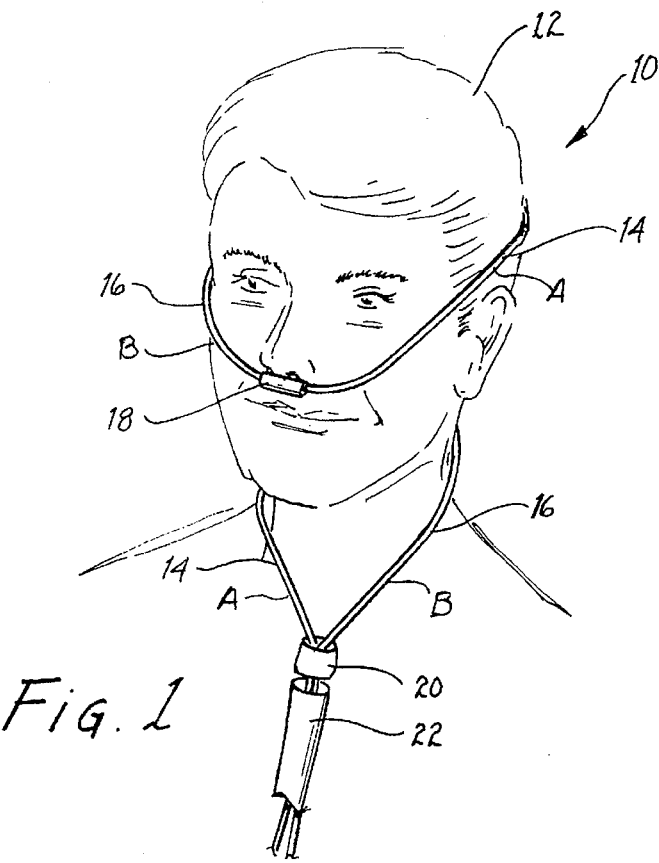
FIG. 1 is a front perspective view of a patient wearing the respiratory device of the instant invention.

Referring to FIG. 1, the respiratory device (hereinafter more simply referred to as the device) of the instant invention is generally designated by reference number 10 and is shown around a head portion of a user 12, or equivalently, patient 12. The device 10 comprises a conduit portion 14 and 16 which passes above the patient's left and right ears and is coupled to the patient's nostrils for supplying a fluid such as oxygen to the patient 12. The device 10 further comprises a coupling portion (24 in FIGS. 2 and 3) contacting a back portion of the user's 12 head and having a cavity (26 in FIG. 3) through which the conduit portion 14 and 16 passes for securely coupling the conduit portion 14 and 16 around a portion of the user's 12 head.

Figure 3:
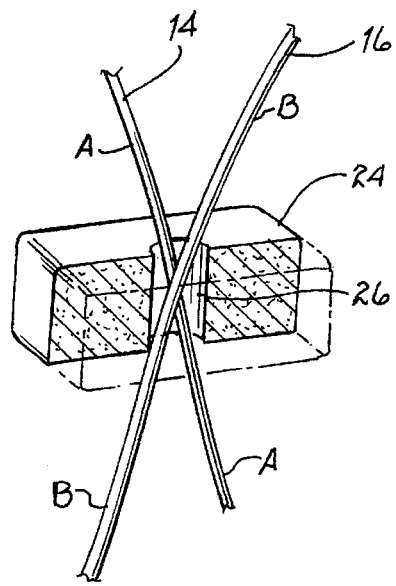
FIG. 3 is a perspective view of the coupling member showing tubular supply lines passing through a cavity therein.
Figure 2:
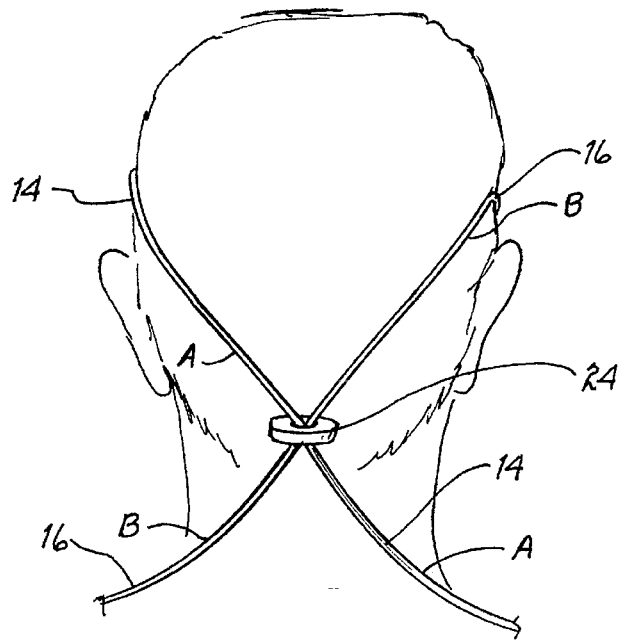
FIG. 2 is a rear perspective view of the patient from FIG. 1.

Again with reference to FIG. 1, note that the conduit portion 14 is labeled with the letter A on the right and left sides of the user 12, above and below the user's ears, respectively. Similarly, the conduit portion 16 is labeled with the letter B on the left and right sides of the user 12, above and below the user's ears, respectively. This is indicative of the fact that the conduit portion 14 and 16 criss-crosses. In particular, the conduit portion 14 and 16 criss-crosses within the cavity 26 (see FIG. 3). This is a key feature of the device 10 because having the conduit portion 14 and 16 criss-cross within the cavity 26, as shown in FIGS. 2 and 3, assists in providing adequate force to hold the device 10 around the patient's head, without the need to wrap the conduit portion 14 and 16 around the patient's ears. In fact, by using the coupling portion 24 with its cavity 26 to hold the criss-cross pattern of the conduit portion 14 and 16, there is sufficient force to hold the device 10 around the patient's head, without having the conduit portion 14 and 16 touch the patient's ears at all. This is a particularly advantageous arrangement of the device 10 in light of the fact that conduit tubes of current respiratory devices must be wrapped around the patient's ears in order to hold the devices in place, but as previously mentioned, at the sacrifice of patient comfort.

The device 10 further includes a nasal cannula 18 coupled to the conduit portion 14 and 16. Such nasal cannula are well known to those skilled in the art for delivering fluids such as oxygen to the nasal passage of a patient. The conduit portion 14 and 16 comprises a plurality of flexible, tubular members independently coupled to the nasal cannula 18. Such flexible, tubular members are well known to those skilled in the art. For example, the Baxter Healthcare Corporation of Valencia, Calif. provides a curved, non-flared tip oxygen cannula with crush resistant tubing under catalog number 001325. In a preferred embodiment of the device 10, tubing similar to that provided by the Baxter product is incorporated into the device 10. In particular, the conduit portion 14 and 16, or equivalently, the tubular members 14 and 16 are substantially flexible, crush-resistant, and tubular in construction, and as alluded to already, such tubular members 14 and 16, as well as the cannula 18 are readily available in the marketplace. Each of the plurality of flexible, tubular members 14 and 16 is greater than 21 inches in length, and in a preferred embodiment of the device 10, each of the tubular members 14 and 16 is approximately 42 inches in length. Tubular members of 21 inches in length, and less, are available; however, such tubular members are too short to be incorporated into the device 10 of the instant invention. Tubular members of 21 inches or less in length are sufficient for the "over-the-ear" style of respiratory device, but are too short for incorporation into the instant invention.

Referring to FIGS. 2 and 3, in a preferred embodiment of the instant invention, the coupling portion 24 comprises a compressible member 24 having the cavity 26 passing therethrough. Member 24 is made from a soft and slightly compressible material. Those skilled in the art therefore recognize that there are several materials, such as a rubber-like material, from which member 24 can be fabricated. The compressible nature of member 24 is very important. In particular, the compressibility of member 24 serves at least two functions. First, since it is slightly compressible, when the patient 12 lays back against the member 24, it is compressed instead of rigidly jabbing the patient's head. Also, when the patient 12 lays back against the member 24, the inner wall surfaces of cavity 26 are squeezed toward each other, at least somewhat, thereby assisting in holding the conduit portion 14 and 16 around the patient's head and the cannula 18 in the patient's nostrils. The criss-crossing of the conduit portion 14 and 16 within the cavity 26 also helps to provide a slight tension across the conduit portion 14 and 16 that aids in holding the conduit portion 14 and 16 around the user's head.

The position of the coupling portion 24 along the conduit portion 14 and 16 is adjustable by sliding the coupling portion 24 along the conduit portion 14 and 16 until a desired position is attained and the conduit portion 14 and 16 is criss-crossed within the cavity 26. Note that the coupling portion 24 is located below the user's left and right ears. Additionally, note that in a preferred embodiment of the instant invention, the fluid supplied to the patient 12 comprises oxygen gas. Lastly, note that in FIG. 3 the cavity 26 comprises a single, tubular cavity 26 in substantial vertical alignment with a vertical axis of the patient's head.

OPERATION

The cannula 18 is coupled to the conduit portion 14 and 16 tubular members. Preferably, each tubular member 14 and 16 is approximately 42 inches in length. The tubular members 14 and 16 are run through the cavity 26 of the compressible member 24 in a criss-crossing pattern as shown in FIG. 3. The cannula 18 is inserted into the patient's nostrils, and the tubular members 14 and 16 are pulled substantially taught, so as to form a comfortable, yet secure cannula-to-nostrills connection. Lastly, the other ends of the tubular members 14 and 16 are draped around the patient's neck, as shown in FIGS. 1 and 2. The ends of the tubular members 14 and 16 are passed through a slide member 20 of a slide adapter. The slide member 20 is slid up toward the patient's neck much like a chin strap to further aid in holding the cannula 18 in the patient's nostrils. The ends of the tubular members 14 and 16 passing through the slide member 20 are coupled to a two-to-one line adapter 22 which, as the name implies, takes the two ends of the tubular members 14 and 16 at one end and couples them to a single tube input at the other end of the adapter 22. Attached to the single tube end of the adapter 22 is a source (not shown) for supplying the needed fluid, such as oxygen.

Although the invention has been particularly shown and described with reference to a preferred embodiment thereof, it will be understood by those skilled in the art that changes in form and detail may be made therein without departing from the spirit and scope of the invention.

What is claimed is:

1. A respiratory device comprising, in combination:
   conduit means adapted to pass above a user's left and right ears and adapted to be coupled to said user's nostrils for supplying a fluid to said user; and
   coupling means adapted to contact a back portion of said user's head and having a cavity through which said conduit means passes for securely coupling said conduit means around a portion of said user's head, said coupling means comprises a compressible member having said cavity passing therethrough, said conduit means having a criss-cross configuration within said cavity.

2. The device of claim 1 further including a nasal cannula coupled to said conduit means.

3. The device of claim 2 wherein said conduit means comprises a plurality of flexible, tubular members independently coupled to said nasal cannula.

4. The device of claim 3 wherein each member of said plurality of flexible, tubular members is greater than 21 inches in length.

5. The device of claim 1 wherein position of said coupling means along said conduit means is adjustable by sliding said coupling means along said conduit means until a desired position is attained.

6. The device of claim 1 wherein said coupling means is located below said user's left and right ears.

7. The device of claim 1 wherein said fluid comprises oxygen gas.

8. The device of claim 1 wherein said cavity comprises a single, tubular cavity in substantial vertical alignment with a vertical axis of said user's head.

9. A method of operating a respiratory device comprising the steps of:

passing conduit means above a user's left and right ears and coupling said conduit means to said user's nostrils for supplying a fluid to said user; and providing coupling means contacting a back portion of said user's head and having a cavity through which said conduit means passes for securely coupling said conduit means around a portion of said user's head, said coupling means comprises a compressible member having said cavity passing therethrough, said conduit means criss-crosses within said cavity.

10. The method of claim 9 further including the step of providing a nasal cannula coupled to said conduit means.

11. The method of claim 10 wherein said conduit means comprises a plurality of flexible, tubular members independently coupled to said nasal cannula.

12. The method of claim 11 wherein each member of said plurality of flexible, tubular members is greater than 21 inches in length.

13. The method of claim 9 wherein position of said coupling means along said conduit means is adjustable by sliding said coupling means along said conduit means until a desired position is attained and said conduit means is criss-crossed within said cavity for holding said conduit means around said portion of said user's head.

14. The method of claim 9 wherein said coupling means is located below said user's left and right ears.

15. The method of claim 9 wherein said fluid comprises oxygen gas.

16. The method of claim 9 wherein said cavity comprises a single, tubular cavity in substantial vertical alignment with a vertical axis of said user's head.

* * * * *